United States Patent
Fukuoka et al.

(10) Patent No.: US 10,494,430 B2
(45) Date of Patent: Dec. 3, 2019

(54) ANTI-ACTIVE GIP ANTIBODY (71) Applicant: Kao Corporation, Chuo-ku, Tokyo (JP)

(72) Inventors: Daisuke Fukuoka, Tokyo (JP); Noriko Osaki, Utsunomiya (JP); Akira Shimotoyodome, Shimotsuke (JP)

(73) Assignee: Kao Corporation, Tokyo (JP)

( * ) Notice: Subject to any disclaimer, the term of this patent is extended or adjusted under 35 U.S.C. 154(b) by 118 days.

(21) Appl. No.: 15/538,534

(22) PCT Filed: Dec. 21, 2015

(86) PCT No.: PCT/JP2015/085700
§ 371 (c)(1),
(2) Date: Jun. 21, 2017

(87) PCT Pub. No.: WO2016/104439
PCT Pub. Date: Jun. 30, 2016

(65) Prior Publication Data
US 2017/0369569 A1  Dec. 28, 2017

(30) Foreign Application Priority Data

Dec. 22, 2014 (JP) .................. 2014-258849

(51) Int. Cl.
*G01N 33/68* (2006.01)
*C07K 16/26* (2006.01)

(52) U.S. Cl.
CPC ............ *C07K 16/26* (2013.01); *G01N 33/68* (2013.01); *C07K 2317/34* (2013.01); *G01N 2333/605* (2013.01)

(58) Field of Classification Search
CPC .......................... C07K 16/26; G01N 2333/605
See application file for complete search history.

(56) References Cited

U.S. PATENT DOCUMENTS

| 2003/0157107 A1 | 8/2003 | Miyawaki et al. |
| 2006/0088550 A1 | 4/2006 | Bachmann et al. |

FOREIGN PATENT DOCUMENTS

| JP | H05-095767 A | 4/1993 |
| JP | 2008-517975 A | 5/2006 |
| JP | 2006-213598 A | 8/2006 |
| JP | 2013-138638 A | 7/2013 |
| WO | WO 01/87341 A1 | 11/2001 |
| WO | WO 2006/045796 A2 | 5/2006 |

OTHER PUBLICATIONS

Rudikoff et al., Proc. Natl. Acad. Sci. 79: 1979-1983, 1982.*
Chamow and Ashkenazi, TIBTECH 14: 52-60, 1996.*
International Search Report (ISR) for PCT/JP2015/085700; I.A. fd: Dec. 21, 2015, dated Feb. 23, 2016 from the Japan Patent Office, Tokyo, Japan.
International Preliminary Report on Patentability (IPRP), Chapter I of the Patent Cooperation Treaty, including the Written Opinion for PCT/JP2015/085700; I.A. fd : Dec. 21, 2015, dated Jun. 27, 2017, by the International Bureau of WIPO, Geneva, Switzerland.
Miyawaki, K. et al., "Inhibition of gastric inhibitory polypeptide signaling prevents obesity," Nat Med. Jul. 2002;8(7):738-42. Epub Jun. 17, 2002 DOI: 10.1038/nm727, Nature Publishing Company, NY.
Troutt, JS et al., "Dual-monoclonal, sandwich immunoassay specific for glucose-dependent insulinotropic peptide$_{1-42}$, the active form of the incretin hormone," Clin Chem. Jun. 2011;57(6):849-55. doi: 10.1373/clinchem.2010.159954. Epub Apr. 22, 2011 American Association for Clinical Chemistry, Washington, DC.
Deacon, CF et al., "Degradation of endogenous and exogenous gastric inhibitory polypeptide in healthy and in type 2 diabetic subjects as revealed using a new assay for the intact peptide," J Clin Endocrinol Metab. Oct. 2000;85(10):3575-81, DOI: 10.1210/jcem. 85.10.6855, Oxford University Press, NY.
Fulurija, A et al., "Vaccination against GIP for the treatment of obesity," PLoS One. Sep. 9, 2008;3(9):e3163, 11 pages, doi: 10.1371/journal.pone.0003163, Public Library of Science, San Francisco, CA.
Hashimoto, T. et al., "Development of a novel assay to measure intact glucose-dependent insulinotropic polypeptide (GIP) levels in human plasma," Diabetes, Jul. 2011, vol. 60, Suppl. 1, p. A600, abstract No. 2257-P0.

* cited by examiner

Primary Examiner — Gyan Chandra
(74) Attorney, Agent, or Firm — Sterne, Kessler, Goldstein & Fox P.L.L.C.

(57) ABSTRACT

Provide is an anti-active GIP antibody which allows accurate detection of active GIP. The present invention provides an anti-active GIP antibody which binds to active GIP and does not substantially bind to nonactive GIP, the antibody recognizing at least one or more amino acids selected from the group consisting of amino acids at $8^{th}$ to $10^{th}$ position of the amino acid sequence represented by SEQ ID NO: 5, and comprising, in an H chain, a region comprising the following amino acid sequence (1) or a conservative sequence modification thereof: EMNPSDGRTHFNE (1).

13 Claims, 3 Drawing Sheets

Specification includes a Sequence Listing.

SEQUENCE LISTING

<160> NUMBER OF SEQ ID NOS: 17

<210> SEQ ID NO 1
<211> LENGTH: 339
<212> TYPE: DNA
<213> ORGANISM: Mus musculus
<220> FEATURE:
<221> NAME/KEY: CDS
<222> LOCATION: (1)..(339)

<400> SEQUENCE: 1

```
cag gtc caa ctg cag cag cct ggg gct gaa ctg gtg aag cct ggg gcc      48
Gln Val Gln Leu Gln Gln Pro Gly Ala Glu Leu Val Lys Pro Gly Ala
  1               5                  10                  15 tca gtg aag ctg tcc tgc aag gct tct ggc tac acc ttc acc agc ttc      96
Ser Val Lys Leu Ser Cys Lys Ala Ser Gly Tyr Thr Phe Thr Ser Phe
             20                  25                  30 tgg atg cac tgg gtg att cag agg cct gga caa ggc ctt gag tgg att     144
Trp Met His Trp Val Ile Gln Arg Pro Gly Gln Gly Leu Glu Trp Ile
         35                  40                  45 gga gag atg aat cct agc gac ggt cgt act cac ttc aat gaa aag ttc     192
Gly Glu Met Asn Pro Ser Asp Gly Arg Thr His Phe Asn Glu Lys Phe
     50                  55                  60
```

| | | | | | | | | | | | | | |
|---|---|---|---|---|---|---|---|---|---|---|---|---|---|
| aag | acc | aag | gcc | aca | ctg | act | ata | gac | aca | tcc | tcc | aac | aca | gcc | tac | 240 |
| Lys | Thr | Lys | Ala | Thr | Leu | Thr | Ile | Asp | Thr | Ser | Ser | Asn | Thr | Ala | Tyr | |
| 65 | | | | 70 | | | | | 75 | | | | | 80 | | |

| atg | gaa | ctc | aac | agc | ctg | aca | tct | gag | gac | tct | gcg | gtc | tat | tac | tgt | 288 |
|---|---|---|---|---|---|---|---|---|---|---|---|---|---|---|---|---|
| Met | Glu | Leu | Asn | Ser | Leu | Thr | Ser | Glu | Asp | Ser | Ala | Val | Tyr | Tyr | Cys | |
| | | | | 85 | | | | | 90 | | | | | 95 | | |

| gca | aga | agg | atg | gag | gac | tgg | ggc | caa | ggg | act | ctg | gtc | act | gtt | tct | 336 |
|---|---|---|---|---|---|---|---|---|---|---|---|---|---|---|---|---|
| Ala | Arg | Arg | Met | Glu | Asp | Trp | Gly | Gln | Gly | Thr | Leu | Val | Thr | Val | Ser | |
| | | | 100 | | | | | 105 | | | | | 110 | | | |

| gca | 339 |
|---|---|
| Ala | |

<210> SEQ ID NO 2
<211> LENGTH: 113
<212> TYPE: PRT
<213> ORGANISM: Mus musculus

<400> SEQUENCE: 2

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Phe
                20                  25                  30

Trp Met His Trp Val Ile Gln Arg Pro Gly Gln Gly Leu Glu Trp Ile
            35                  40                  45

Gly Glu Met Asn Pro Ser Asp Gly Arg Thr His Phe Asn Glu Lys Phe
        50                  55                  60

Lys Thr Lys Ala Thr Leu Thr Ile Asp Thr Ser Ser Asn Thr Ala Tyr
65                  70                  75                  80

Met Glu Leu Asn Ser Leu Thr Ser Glu Asp Ser Ala Val Tyr Tyr Cys
                85                  90                  95

Ala Arg Arg Met Glu Asp Trp Gly Gln Gly Thr Leu Val Thr Val Ser
            100                 105                 110

Ala

<210> SEQ ID NO 3
<211> LENGTH: 324
<212> TYPE: DNA
<213> ORGANISM: Mus musculus
<220> FEATURE:
<221> NAME/KEY: CDS
<222> LOCATION: (1)..(324)

<400> SEQUENCE: 3

| gac | atc | aag | atg | acc | cag | tct | cca | tct | tcc | atg | tat | gca | tct | cta | gga | 48 |
|---|---|---|---|---|---|---|---|---|---|---|---|---|---|---|---|---|
| Asp | Ile | Lys | Met | Thr | Gln | Ser | Pro | Ser | Ser | Met | Tyr | Ala | Ser | Leu | Gly | |
| 1 | | | | 5 | | | | | 10 | | | | | 15 | | |

| gag | aga | gtc | act | atc | act | tgc | aag | gcg | agt | cag | gac | att | aat | agc | tat | 96 |
|---|---|---|---|---|---|---|---|---|---|---|---|---|---|---|---|---|
| Glu | Arg | Val | Thr | Ile | Thr | Cys | Lys | Ala | Ser | Gln | Asp | Ile | Asn | Ser | Tyr | |
| | | | 20 | | | | | 25 | | | | | 30 | | | |

| tta | ggc | tgg | ttc | cag | cag | aaa | cca | ggg | aaa | tct | cct | aag | acc | ctg | ata | 144 |
|---|---|---|---|---|---|---|---|---|---|---|---|---|---|---|---|---|
| Leu | Gly | Trp | Phe | Gln | Gln | Lys | Pro | Gly | Lys | Ser | Pro | Lys | Thr | Leu | Ile | |
| | | | 35 | | | | | 40 | | | | | 45 | | | |

| tat | ggt | gca | aac | aga | ttg | gta | gat | ggg | gtc | cca | tca | agg | ttc | agt | ggc | 192 |
|---|---|---|---|---|---|---|---|---|---|---|---|---|---|---|---|---|
| Tyr | Gly | Ala | Asn | Arg | Leu | Val | Asp | Gly | Val | Pro | Ser | Arg | Phe | Ser | Gly | |
| | 50 | | | | | 55 | | | | | 60 | | | | | |

| agt | gga | tct | ggg | caa | gat | tac | tct | ctc | acc | atc | agc | agc | ctg | gag | tat | 240 |
|---|---|---|---|---|---|---|---|---|---|---|---|---|---|---|---|---|
| Ser | Gly | Ser | Gly | Gln | Asp | Tyr | Ser | Leu | Thr | Ile | Ser | Ser | Leu | Glu | Tyr | |
| 65 | | | | 70 | | | | | 75 | | | | | 80 | | |

| gac | gat | atg | gga | ata | tat | tat | tgt | cta | cag | tat | gat | gag | ttt | ccg | ctc | 288 |
|---|---|---|---|---|---|---|---|---|---|---|---|---|---|---|---|---|
| Asp | Asp | Met | Gly | Ile | Tyr | Tyr | Cys | Leu | Gln | Tyr | Asp | Glu | Phe | Pro | Leu | |

```
                85                  90                  95
acc ttc ggt gct ggg acc aag ctg gag ctg aaa cgg                      324
Thr Phe Gly Ala Gly Thr Lys Leu Glu Leu Lys Arg
            100                 105

<210> SEQ ID NO 4
<211> LENGTH: 108
<212> TYPE: PRT
<213> ORGANISM: Mus musculus

<400> SEQUENCE: 4

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Gly Trp Phe Gln Gln Lys Pro Gly Lys Ser Pro Lys Thr Leu Ile
        35                  40                  45

Tyr Gly Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Asp Asp Met Gly Ile Tyr Tyr Cys Leu Gln Tyr Asp Glu Phe Pro Leu
                85                  90                  95

Thr Phe Gly Ala Gly Thr Lys Leu Glu Leu Lys Arg
            100                 105

<210> SEQ ID NO 5
<211> LENGTH: 42
<212> TYPE: PRT
<213> ORGANISM: Homo sapiens

<400> SEQUENCE: 5

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 6
<211> LENGTH: 67
<212> TYPE: DNA
<213> ORGANISM: Artificial Sequence
<220> FEATURE:
<223> OTHER INFORMATION: synthetic oligonucleotide

<400> SEQUENCE: 6
ctaatacgac tcactatagg gcaagcagtg gtatcaacgc agagtctaat acgactcact      60
atagggc                                                               67

<210> SEQ ID NO 7
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 7
gggaartarc ccttgaccag gca                                             23
```

-continued

```
<210> SEQ ID NO 8
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 8
gggaartagc ctttgacaag gca                                              23

<210> SEQ ID NO 9
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 9
cactgccatc aatcttccac ttgaca                                           26

<210> SEQ ID NO 10
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 10
cgccagggtt ttcccagtca cgac                                             24

<210> SEQ ID NO 11
<211> LENGTH: 13
<212> TYPE: PRT
<213> ORGANISM: Mus musculus

<400> SEQUENCE: 11

Glu Met Asn Pro Ser Asp Gly Arg Thr His Phe Asn Glu
1               5                   10

<210> SEQ ID NO 12
<211> LENGTH: 10
<212> TYPE: PRT
<213> ORGANISM: Artificial Sequence
<220> FEATURE:
<223> OTHER INFORMATION: synthetic peptide

<400> SEQUENCE: 12

Tyr Ala Glu Gly Thr Phe Ile Ser Asp Tyr
1               5                   10

<210> SEQ ID NO 13
<211> LENGTH: 9
<212> TYPE: PRT
<213> ORGANISM: Artificial Sequence
<220> FEATURE:
<223> OTHER INFORMATION: synthetic peptide

<400> SEQUENCE: 13

Tyr Ala Glu Gly Thr Phe Ile Ser Asp
1               5

<210> SEQ ID NO 14
<211> LENGTH: 8
<212> TYPE: PRT
<213> ORGANISM: Artificial Sequence
<220> FEATURE:
<223> OTHER INFORMATION: synthetic peptides
```

```
<400> SEQUENCE: 14

Tyr Ala Glu Gly Thr Phe Ile Ser
1               5

<210> SEQ ID NO 15
<211> LENGTH: 7
<212> TYPE: PRT
<213> ORGANISM: Artificial Sequence
<220> FEATURE:
<223> OTHER INFORMATION: synthetic peptides

<400> SEQUENCE: 15

Tyr Ala Glu Gly Thr Phe Ile
1               5

<210> SEQ ID NO 16
<211> LENGTH: 6
<212> TYPE: PRT
<213> ORGANISM: Artificial Sequence
<220> FEATURE:
<223> OTHER INFORMATION: synthetic peptides

<400> SEQUENCE: 16

Tyr Ala Glu Gly Thr Phe
1               5

<210> SEQ ID NO 17
<211> LENGTH: 10
<212> TYPE: PRT
<213> ORGANISM: Artificial Sequence
<220> FEATURE:
<223> OTHER INFORMATION: synthetic peptides

<400> SEQUENCE: 17

Tyr Ala Glu Gly Thr Phe Val Asn Leu Val
1               5                   10
```

ANTI-ACTIVE GIP ANTIBODY

REFERENCE TO SEQUENCE LISTING SUBMITTED ELECTRONICALLY

The content of the electronically submitted substitute sequence listing, file name 2537_1340001_Seqlisting_ST25.txt, size 8,761 bytes; and date of creation Sep. 3, 2019, filed herewith, is incorporated herein by reference in its entirety.

FIELD OF THE INVENTION

The present invention relates to an antibody specifically reacting with active GIP and use thereof.

BACKGROUND OF THE INVENTION

GIP (gastric inhibitory polypeptide or glucose-dependent insulinotropic polypeptide) is a gastrointestinal hormone belonging to the glucagon/secretin family. GIP is called incretin, as with GLP-1 (glucagon-like peptide 1), and is secreted by K cells present in the small intestine upon intake of lipids or carbohydrates.

GIP is known to promote insulin secretion from pancreatic β cells and to enhance the uptake of glucose into fat cells in the presence of insulin. Therefore, the action of GIP is considered to be partly responsible for obesity. It has been reported that obesity is actually suppressed by inhibiting the functions of GIP (Non Patent Literature 1).

It has been further reported that GIP is partly responsible for insulin resistance (Non Patent Literature 1). When insulin resistance occurs, glucose-absorbing effects mediated by insulin are reduced, consequently causing hyperinsulinemia. It is recognized that hyperinsulinemia is a primary cause leading to the occurrence of various lifestyle-related diseases including obesity. The prevention or amelioration of insulin resistance is also important in terms of the risk reduction of the lifestyle-related diseases.

GIP is also known to have inhibitory effect of gastric secretion or gastric motility (Patent Literatures 1 to 3). The suppression of elevation of GIP is presumably effective for the enhancement of digestibility after eating or the amelioration of heavy feeling in the stomach.

Thus, the measurement of the concentration of GIP in blood is important for the evaluation of such diseases or therapeutic drugs therefor.

GIP is known to include an active form having physiological activity and a nonactive form lacking physiological activity. Specifically, in humans, prepro-GIP is processed into active GIP (also referred to as "GIP(1-42)") in K cells distributed in the stomach, the duodenum, and the upper small intestine. Then, N-terminal 2 amino acids of the active GIP are cleaved off by DPP-4 to form nonactive GIP (also referred to as "GIP(3-42)"). Thus, in the quantification of in vivo GIP, the mere measurement of the total amount of the active and nonactive forms does not permit accurate determination of the effects of therapeutic drugs, the risk of lifestyle-related diseases, etc.

An active GIP quantification kit (Immuno-Biological Laboratories Co, Ltd. (IBL)) is commercially available as a conventional approach for measuring active GIP. The problems of this kit are that 1) active GIP concentrations in blood after eating are higher than the quantification limit of the kit, 2) the coefficient of variation exceeds 10% for different dilution ratios, and 3) a higher dilution ratio leads to a higher measurement level. Recently, it has been reported that active GIP having a concentration of 5 to 4,000 pg/mL can be quantified by ELISA using an anti-active GIP monoclonal antibody prepared by using, as an immunogen, a peptide consisting of N-terminal 6 amino acid residues of GIP(1-42) (Non Patent Literature 2). It has also been reported that active GIP having a concentration of 7 to 500 pg/mL can be quantified by ELISA using an anti-active GIP monoclonal antibody prepared by using, as an immunogen, a peptide consisting of N-terminal 7 amino acid residues of GIP(1-42) (Patent Literature 4).

(Patent Literature 1) WO 01/87341
(Patent Literature 2) JP2006-213598A
(Patent Literature 3) JP5-95767A
(Patent Literature 4) JP2013-138638A
(Non Patent Literature 1) Miyawaki K et al., Nat Med. 8 (7): 738-42, 2002
(Non Patent Literature 2) Jason S. Troutt et al., Clinical Chemistry, 57 (6): 849-855 (2011)

SUMMARY OF THE INVENTION

The present invention relates to the following 1) to 3):

1) An anti-active GIP antibody which binds to active GIP and does not substantially bind to nonactive GIP, the antibody recognizing at least one or more amino acids selected from the group consisting of amino acids at positions 8 to 10 of the amino acid sequence represented by SEQ ID NO: 5, and comprising, in an H chain, a region comprising the following amino acid sequence (1) or a conservative sequence modification thereof:

EMNPSDGRTHFNE (1) (SEQ ID NO:11).

2) A method for detecting or measuring active GIP using an antibody according to 1).

3) A reagent for detection or measurement of active GIP, comprising an antibody according to 1).

BRIEF DESCRIPTION OF THE DRAWINGS

FIGS. 2A and 2B show GIP(1-42) in blood and a total GIP level in blood, respectively, after taking of a control diet or a test diet (N=5, crossover test on the same test subjects). FIG. 2C shows the ratio of GIP(1-42) to total GIP after eating (%).

DETAILED DESCRIPTION OF THE INVENTION

The present invention relates to the provision of an anti-active GIP antibody which allows accurate detection of active GIP.

The present inventors have conducted various studies to obtain an antibody specifically recognizing active GIP, and consequently successfully obtained a novel anti-active GIP antibody which recognizes an epitope different from that for previous antibodies and has high specificity.

By using the antibody of the present invention, active GIP can be detected in distinction from nonactive GIP with high accuracy. Thus, the present invention enables, for example, measurement of active GIP in a biological sample, detection of an abnormal active GIP level, and evaluation of response to a therapeutic drug using active GIP as an indicator. Moreover, it becomes possible to estimate DPP-4 by calculating the ratio of active GIP to total GIP.

In the present invention, the "active GIP" means mammalian active GIP and is preferably human active GIP. The human active GIP is a peptide consisting of 42 amino acids ("GIP(1-42)") (SEQ ID NO: 5). On the other hand, the "nonactive GIP" means a peptide wherein 2 amino acids (YA) at the N-terminal of the active GIP are cleaved ("GIP(3-42)").

The anti-active GIP antibody according to the present invention is an antibody which binds to active GIP and does not substantially bind to nonactive GIP.

A test antibody can be confirmed to not substantially bind to nonactive GIP, by measuring its binding to the nonactive GIP using a method such as Western blotting, immunoprecipitation, immunohistochemical staining, or ELISA. Specifically, when the amount of the test antibody bound with the nonactive GIP is 10% or less at most, preferably 5% or less, more preferably 1% or less, even more preferably 0.1% or less with respect to the amount of the test antibody bound with the active GIP as 100%, it can be concluded that this test antibody does "not substantially bind to nonactive GIP".

Measurement by sandwich ELISA can be performed using, for example, an anti-total GIP antibody as a capture antibody and a biotinylated anti-active GIP monoclonal antibody as a detection antibody for a nonactive GIP solution.

Also, the antibody of the present invention is an antibody which recognizes amino acid(s) at or subsequent to the eighth position from the N terminus of the active GIP (SEQ ID NO: 5), and is an antibody which recognizes at least one or more amino acids selected from the group consisting of amino acids at positions 8 to 10 (SDY).

Further, the antibody of the present invention comprises, in an H chain, a region comprising the following amino acid sequence (1) or a conservative sequence modification thereof:

EMNPSDGRTHFNE (1) (SEQ ID NO:11).

The alphabet letters in the sequence (1) mean the one-letter codes of amino acids. The sequence is described in order from the N terminus toward the C terminus. In this context, I represents isoleucine, L represents leucine, F represents phenylalanine, V represents valine, A represents alanine, T represents threonine, D represents aspartic acid, Q represents glutamine, E represents glutamic acid, M represents methionine, N represents asparagine, P represents proline, S represents serine, G represents glycine, R represents arginine, and H represents histidine.

In the present invention, the "conservative sequence modification" means an amino acid modification which does not significantly affect or alter the reactivity of the antibody consisting of an unmodified amino acid sequence. Such a conservative sequence modification includes substitution, addition, and deletion of 1 to several, preferably 1 to 3, more preferably 1 amino acid(s). Examples of an amino acid sequence derived by the conservative sequence modification include an amino acid sequence having 90% or higher, preferably 95% or higher, more preferably 98% or higher sequence identity to the unmodified amino acid sequence. The modification can be introduced to the antibody of the present invention by a standard technique known in the art, such as site-directed mutagenesis or PCR-mediated mutagenesis. Examples of the conservative amino acid substitution include the substitution of an amino acid residue by an amino acid residue having a similar side chain (a member of the same amino acid residue family). The amino acid residue family is defined in the art and includes amino acids having basic side chains (e.g., lysine, arginine, and histidine), acidic side chains (e.g., aspartic acid and glutamic acid), uncharged polar side chains (e.g., glycine, asparagine, glutamine, serine, threonine, tyrosine, cysteine, and tryptophan), nonpolar side chains (e.g., alanine, valine, leucine, isoleucine, proline, phenylalanine, and methionine), β-branched side chains (e.g., threonine, valine, and isoleucine), and aromatic side chains (e.g., tyrosine, phenylalanine, tryptophan, and histidine).

The amino acid sequence (1) encodes a region consisting of 13 amino acid residues from 50th to 62th position of the amino acid sequence represented by SEQ ID NO: 2 which represents an H chain variable region.

The antibody of the present invention may be a fragment of the antibody, for example, F(ab')$_2$, F(ab'), single-chain Fv (scFv), disulfide-stabilized Fv (dsFv) in which cysteine residues replaced for amino acid residues in VH and VL are bound via a disulfide bond, or a polymer thereof, or a dimerized V region (diabody) which is an scFv dimer, as long as the fragment has the reactivity described above. The fragment of the antibody also includes a peptide comprising a portion of the anti-active GIP antibody as long as the peptide has the reactivity described above, and specifically includes a peptide which has a portion of the amino acid sequence constituting the antibody and has the reactivity described above.

The antibody of the present invention is not particularly limited by its immunoglobulin class. The immunoglobulin class may be any of IgG, IgM, IgA, IgE, IgD, and IgY and is preferably IgG. The antibody of the present invention encompasses even an antibody of any isotype.

The antibody of the present invention may be any of a nonhuman animal antibody, a human-type chimeric antibody, a humanized antibody, and a human antibody. Examples of the nonhuman animal antibody include mouse, rat, hamster, and guinea pig antibodies. A mouse antibody is preferred.

In this context, the "human-type chimeric antibody" is an antibody genetically engineered such that the constant regions of a nonhuman animal-derived antibody specifically binding to active GIP are converted to the corresponding constant regions of a human antibody, and is preferably a human-mouse chimeric antibody. The "humanized antibody" is an antibody genetically engineered such that a primary structure except for the H chain and L chain complementarity-determining regions (CDRs) of a nonhuman animal-derived antibody specifically binding to active GIP is converted to the corresponding primary structure of a human antibody. The "human antibody" means a human antibody which is an expression product of a completely human-derived antibody gene.

Preferably, the antibody of the present invention further comprises, as an H chain variable region, a region comprising the amino acid sequence represented by SEQ ID NO: 2 or a conservative sequence modification thereof.

Preferably, the antibody of the present invention further comprises, as an H chain variable region, a region comprising the amino acid sequence represented by SEQ ID NO: 2 or a conservative sequence modification thereof, and, as an L chain variable region, a region comprising the amino acid sequence represented by SEQ ID NO: 4 or a conservative sequence modification thereof.

According to another aspect, the present invention provides an antibody constituent and a gene thereof shown in 1) and 2) below. A polypeptide (H chain variable region) consisting of the amino acid sequence represented by SEQ ID NO: 2 or a conservative sequence modification thereof is particularly preferred as an antibody fragment which functions as the antibody of the present invention, since it comprises the amino acid sequence represented by the above described (1).

1) The following polypeptide and a gene encoding the polypeptide:

(a) a polypeptide consisting of the amino acid sequence represented by SEQ ID NO: 2, or a polypeptide having an amino acid sequence having 90% or higher, more preferably 95% or higher, further preferably 98% or higher identity to the amino acid sequence, the polypeptide functioning as an antibody which binds to active GIP and does not substantially bind to nonactive GIP; and (b) DNA consisting of the nucleotide sequence represented by SEQ ID NO: 1, or DNA consisting of a nucleotide sequence having 90% or higher, more preferably 95% or higher, further preferably 98% or higher identity to the nucleotide sequence, the DNA encoding a polypeptide functioning as an antibody which binds to active GIP and does not substantially bind to nonactive GIP.

2) The following polypeptide and a gene encoding the polypeptide:

(c) a polypeptide consisting of the amino acid sequence represented by SEQ ID NO: 4, or a polypeptide having an amino acid sequence having 90% or higher, more preferably 95% or higher, further preferably 98% or higher identity to the amino acid sequence, the polypeptide functioning as an antibody which binds to active GIP and does not substantially bind to nonactive GIP; and (d) DNA consisting of the nucleotide sequence represented by SEQ ID NO: 3, or DNA consisting of a nucleotide sequence having 90% or higher, more preferably 95% or higher, further preferably 98% or higher identity to the nucleotide sequence, the DNA encoding a polypeptide functioning as an antibody which binds to active GIP and does not substantially bind to nonactive GIP.

Examples of the DNA consisting of a nucleotide sequence having 90% or higher identity to the nucleotide sequence represented by SEQ ID NO: 1 or 3 include DNA hybridizing under stringent conditions to the nucleotide sequence represented by SEQ ID NO: 1 or 3. In this case, examples of the hybridization conditions include conditions involving hybridization at 42° C. in 6×SSC (0.9 M NaCl and 0.09 M trisodium citrate) or 6×SSPE (3 M NACl, 0.2 M NaH$_2$PO$_4$, and 20 mM EDTA.2Na, pH 7.4) followed by washing with 0.5×SSC at 42° C.

In the present invention, the identity between amino acid sequences or nucleotide sequences refers to the ratio (%) of the number of positions of identical amino acid residues or bases between two amino acid sequences or nucleotide sequences to the number of full-length amino acid residues or bases when the two sequences are aligned. Specifically, the identity is calculated by, for example, the Lipman-Pearson method (Science, 227, 1435, (1985)) and can be calculated by analysis using the Search homology program of gene information processing software Genetyx-Win (Ver. 5.1.1; Software Knowledge Inc) and Unit size to compare (ktup) set to 2.

Examples of the anti-active GIP antibody comprising, as an H chain variable region, a region consisting of the amino acid sequence represented by SEQ ID NO: 2, and, as an L chain variable region, a region consisting of the amino acid sequence represented by SEQ ID NO: 4 include a monoclonal antibody produced from a hybridoma 9B9H5-B9 line shown in Example 1 described later.

The anti-active GIP antibody of the present invention can be obtained as a monoclonal antibody by using an approach known in the art. A mammal-derived monoclonal antibody encompasses a monoclonal antibody produced from a hybridoma, and a monoclonal antibody produced by designing an antibody gene or an antibody fragment gene and using a well-known genetic engineering approach.

Examples of the genetic engineering approach include the production of a single-chain recombinant antibody protein (scFv) having the ability to bind to the antibody, for example, by inserting each of DNA encoding an H chain variable region (e.g., DNA consisting of the nucleotide sequence represented by SEQ ID NO: 1) and DNA encoding an L chain variable region (e.g., DNA consisting of the nucleotide sequence represented by SEQ ID NO: 3) to downstream of a promoter in an appropriate vector to prepare recombinant vectors, transfecting host cells with the vectors, producing an H chain and an L chain from the resulting transformants, and linking the H chain and the L chain via a possible peptide; or by linking DNA encoding an H chain variable region (e.g., DNA consisting of the nucleotide sequence represented by SEQ ID NO: 1) and DNA encoding an L chain variable region (e.g., DNA consisting of the nucleotide sequence represented by SEQ ID NO: 3) via DNA encoding a linker known in the art, inserting the resulting DNA construct to downstream of a promoter in an appropriate vector to prepare a recombinant vector, and expressing the antibody in host cells (see e.g., MacCfferty, J. et al., Nature, 348, 552-554, 1990; and Tim Clackson et al., Nature, 352, 642-628, 1991). Alternatively, the genetic engineering approach may be production by linking DNAs encoding variable regions and DNAs encoding constant regions, followed by expression. In this case, the constant regions and the variable regions may be derived from the same antibody or may be derived from different antibodies.

The introduction of an amino acid mutation for preparing a functionally equivalent polypeptide as described above can be performed by, for example, site-directed mutagenesis.

An anti-active GIP antibody-producing hybridoma can be prepared by basically using a technique known in the art as follows:

For example, active GIP or a peptide having an N-terminal amino acid sequence thereof (a peptide consisting of an amino acid sequence from positions 1 to 15 of SEQ ID NO: 5) is bound, if necessary, to an appropriate carrier protein, for example, keyhole limpet hemocyanin (KLH) or bovine serum albumin so as to enhance its immunogenicity. A nonhuman mammal can be immunized with the resulting antigen for hybridization preparation. The active GIP or the peptide for use as a sensitizing antigen (immunogen) can be prepared by a genetic engineering approach or chemical synthesis.

The mammal to be immunized with the sensitizing antigen is not particularly limited and is preferably selected in consideration of compatibility with mammalian myeloma cells serving as parent cells for use in cell fusion. In general, a rodent animal, for example, a mouse, a rat, or a hamster is used.

The immunization of the animal with the sensitizing antigen is performed according to a method known in the art. For example, the immunization is performed by the intraperitoneal or subcutaneous injection of the sensitizing antigen to the mammal. Specifically, the sensitizing antigen is diluted or suspended into an appropriate amount with PBS (phosphate-buffered saline), physiological saline, or the like, and this dilution or suspension is mixed, if desired, with an appropriate amount of a usual adjuvant, for example, a complete Freund's adjuvant, and thereby emulsified. The emulsion is administered, for example, subcutaneously, intracutaneously, or intraperitoneally, to the animal for priming. Then, similar operation is repeated according to the need. The dose of the antigen is appropriately determined according to the administration route and the animal species. The usual dose is preferably on the order of 10 μg to 1 mg per dose. After confirmation of elevation in the desired antibody level in the serum of the animal thus immunized, immunocytes are isolated from the mammal having an elevated antibody level and subjected to in cell fusion. Particularly preferred examples of the immunocytes for the cell fusion include spleen cells.

Various cell lines have already been constructed as mammalian myeloma cells serving as the other parent cells to be fused with the immunocytes, and, for example, P3X63, NS-1, MPC-11, or SP2/0 is appropriately used.

The cell fusion of the immunocytes with the myeloma cells can be performed according to a method known in the art, for example, the method of Kohler et al. (Kohler et al., Nature, vol. 256, p. 495-497 (1975)). Specifically, fused cells (hybridomas) are formed by mixing the immunocytes and the myeloma cells in a nutrient medium, such as a RPMI1640 medium or a MEM medium, supplemented with an auxiliary such as dimethyl sulfoxide, if desired, in the presence of a cell fusion promoter such as polyethylene glycol (PEG having an average molecular weight of 1,000 to 6,000; 30 to 60% concentration) or hemagglutinating virus of Japan (HVJ).

The hybridomas formed by the fusion are cultured for 1 to 7 days in a selective medium such as a medium containing hypoxanthine, thymidine, and aminopterin (HAT medium) and thereby separated from unfused cells. From the obtained hybridomas, a hybridoma producing the antibody of interest (antibody which binds to active GIP and does not substantially bind to nonactive GIP) is further selected.

The selected hybridoma is prepared into a single clone according to a limiting dilution method known in the art and established as a monoclonal antibody-producing hybridoma.

A method known in the art can be used as a method for detecting the activity of the antibody produced by the hybridoma. Examples thereof include ELISA, agglutination, and radioimmunoassay.

To obtain monoclonal antibody from the generated hybridoma, for example, methods as follows are adopted: a method which involves culturing the hybridoma according to a usual method and obtaining the monoclonal antibody as the culture supernatant, or a method which involves administering the hybridoma to a mammal compatible therewith, proliferating the hybridoma, and obtaining the monoclonal antibody as an ascetic fluid thereof.

The antibody can be purified by a purification approach known in the art, such as salting-out, gel filtration, ion-exchange chromatography, or affinity chromatography.

The anti-active GIP antibody of the present invention can be used in an arbitrary immunological measurement method to specifically detect or measure active GIP in a specimen. More specifically, by bringing the anti-active GIP antibody of the present invention into contact with the specimen and detecting the binding of the specimen to the antibody and immunologically measuring the level of active GIP, the active GIP in the biological sample or in vivo can be detected or measured.

This enables, for example, measurement of active GIP in a biological sample, detection of an abnormal active GIP level, and evaluation of response to a therapeutic drug with active GIP as an index.

In this context, examples of the immunological measurement method can include, but are not particularly limited to: immunohistological staining, fluorescent antibody, adsorption, and neutralization methods as qualitative analyses; and ELISA, radioimmunoassay, and Western blotting as quantitative analyses. Among these methods, ELISA is preferably used because of its convenience. ELISA and radioimmunoassay include competition, sandwich, and direct adsorption methods.

The competition method involves binding an anti-active GIP antibody to a plate for assay and adding thereto a sample together with a given concentration of active GIP labeled with an enzyme (e.g., calf intestinal alkaline phosphatase (CIAP) or horseradish peroxidase), a radioisotope, or the like. Active GIP in the sample and the labeled active GIP compete with each other for binding to the anti-active GIP antibody. The labeled active GIP binds to the anti-active GIP antibody according to the concentration of the active GIP in the sample. Therefore, the concentration of the active GIP in the sample can be estimated from the amount of the antibody bound to the labeled active GIP.

The sandwich method employs an anti-GIP antibody and a labeled anti-active GIP antibody. The anti-GIP antibody is preferably an antibody differing in epitope from the anti-active GIP antibody. Examples of such an antibody include an anti-total GIP antibody. A preferred method employs an immobilized anti-GIP antibody and a labeled anti-active GIP antibody.

The immobilized anti-GIP antibody is preferably an antibody immobilized on an insoluble support such as a polystyrene plate, a latex particle, a magnetic particle, a glass fiber membrane, a nylon membrane, a nitrocellulose membrane, or a cellulose acetate membrane.

For example, a radioisotope (e.g., $^{32}P$, $^{35}S$, and $^{3}H$), an enzyme (e.g., peroxidase, alkaline phosphatase, and luciferase), a protein (e.g., avidin), a low-molecular compound (e.g., biotin), a fluorescent material (e.g., FITC), a chemiluminescent material (e.g. acridinium), a latex particle (e.g., a colored latex particle and a fluorescent latex particle), a metal (e.g., noble metals such as gold, silver, and platinum) colloid particle, or a carbon atom can be used as a label for the labeled anti-active GIP antibody.

The direct adsorption method (direct method) is a method which involves adsorbing an antigen onto a solid phase and reacting the antigen with a labeled anti-active GIP antibody.

The detection of the active GIP in the specimen (biological sample) is performed by reacting the active GIP in the sample with the immobilized anti-GIP antibody. In the case of, for example, the sandwich method, the detection can be performed by reacting a sample-containing solution with the immobilized anti-GIP antibody, followed by reaction with the labeled antibody, or by reacting the sample-containing solution with the immobilized anti-GIP antibody and the labeled antibody at the same time. After the completion of the reaction, the amount of the label in a complex formed by the active GIP in the sample, the immobilized anti-GIP antibody, and the labeled antibody can be measured to measure the amount of the active GIP in the sample. The measurement of the amount of the label can be performed by an approach according to the type of the labeling material. In the case of using, for example, an enzyme as the label, a substrate is added after the reaction, and the enzyme activity is measured. In the case of using a fluorescent (including a fluorescent latex particle) or chemiluminescent material as the label, a signal is measured under conditions which cause no quenching. As for a colored latex particle, a metal colloid particle, and a carbon particle, etc., a signal is measured visually or on the basis of reflected light or the like.

A detection or measurement reagent (kit) comprising the anti-active GIP antibody of the present invention is used in a method for measuring or detecting active GIP in a specimen using the anti-active GIP antibody of the present invention. This reagent is intended for the qualitative, quantitative, or semiquantitative detection or measurement of active GIP in a biological sample (e.g., tissues, blood, plasma, serum, and lymph) collected from a test subject, or in vivo.

The detection or measurement reagent comprising the anti-active GIP antibody is preferably configured to comprise the labeled anti-active GIP antibody of the present invention as well as, for example, a diluting solution for specimens, an immobilized anti-GIP antibody, a reaction substrate, and an coloring reagent if necessary, reagent for reaction termination, standard antigen reagent, reagent for sample pretreatment, and blocking reagent. The anti-active GIP antibody may be contained in or immobilized on a resin, a membrane, a film, a container, or the like, or dissolved in a solvent.

In relation to the embodiments mentioned above, the present invention discloses the following aspects:

<1> An anti-active GIP antibody which binds to active GIP and does not substantially bind to nonactive GIP, the antibody recognizing at least one or more amino acids selected from the group consisting of amino acids from 8th to 10th position of the amino acid sequence represented by SEQ ID NO: 5, and comprising, in an H chain, a region comprising the following amino acid sequence (1) or a conservative sequence modification thereof:
EMNPSDGRTHFNE (1) (SEQ ID NO:11).

<2> The antibody according to <1>, wherein the antibody comprises, as an H chain variable region, a region comprising the amino acid sequence represented by SEQ ID NO: 2 or a conservative sequence modification thereof.

<3> The antibody according to <2>, wherein an amino acid sequence derived by the conservative sequence modification has 90% or higher identity to the amino acid sequence represented by SEQ ID NO: 2.

<4> The antibody according to <1> or <2>, wherein the antibody comprises, as an H chain variable region, a region comprising the amino acid sequence represented by SEQ ID NO: 2 or a conservative sequence modification thereof, and, as an L chain variable region, a region comprising the amino acid sequence represented by SEQ ID NO: 4 or a conservative sequence modification thereof.

<5> The antibody according to <4>, wherein an amino acid sequence derived by the conservative sequence modification from the amino acid sequence represented by SEQ ID NO: 2 has 90% or higher identity to the amino acid sequence represented by SEQ ID NO: 2, and an amino acid sequence derived by the conservative sequence modification from the amino acid sequence represented by SEQ ID NO: 4 has 90% or higher identity to the amino acid sequence represented by SEQ ID NO: 4.

<6> A method for detecting or measuring active GIP using an antibody according to any of <1> to <5>.

<7> A method for detecting or measuring active GIP in a sample, comprising the following steps 1) and 2):
1) contacting an immobilized anti-GIP antibody and a labeled antibody according to any of <1> to <5>, either together or separately, with a sample-containing solution; and 2) measuring the amount of the label in a complex formed by the active GIP in the sample, the immobilized anti-GIP antibody, and the labeled antibody.

<8> A reagent for detection or measurement of active GIP, comprising an antibody according to any of <1> to <5>.

<9> The following polypeptide and a gene encoding the polypeptide:
(a) a polypeptide consisting of the amino acid sequence represented by SEQ ID NO: 2, or a polypeptide having an amino acid sequence having 90% or higher, more preferably 95% or higher, further preferably 98% or higher identity to the amino acid sequence, the polypeptide functioning as an antibody which binds to active GIP and does not substantially bind to nonactive GIP; and
(b) DNA consisting of the nucleotide sequence represented by SEQ ID NO: 1, or DNA consisting of a nucleotide sequence having 90% or higher, more preferably 95% or higher, further preferably 98% or higher identity to the nucleotide sequence, the DNA encoding a polypeptide functioning as an antibody which binds to active GIP and does not substantially bind to nonactive GIP.

<10> The following polypeptide and a gene encoding the polypeptide:
(c) a polypeptide consisting of the amino acid sequence represented by SEQ ID NO: 4, or a polypeptide having an amino acid sequence having 90% or higher, more preferably 95% or higher, further preferably 98% or higher identity to the amino acid sequence, the polypeptide functioning as an antibody which binds to active GIP and does not substantially bind to nonactive GIP; and
(d) DNA consisting of the nucleotide sequence represented by SEQ ID NO: 3, or DNA consisting of a nucleotide sequence having 90% or higher, more preferably 95% or higher, further preferably 98% or higher identity to the nucleotide sequence, the DNA encoding a polypeptide functioning as an antibody which binds to active GIP and does not substantially bind to nonactive GIP.

EXAMPLES

Example 1 Preparation of Antibody

1) Synthesis of Peptide for Immunization

The N-terminal 15 amino acids of active GIP (GIP(1-15)) were PEGylated and then chemically bound to KLH to prepare KLH-bound PEGylated GIP(1-15), which was used as an immunizing antigen. PEGylated N-terminal 15 amino acids of active GIP (GIP(1-15)) were used as antigen (1) for measurement, and PEGylated N-terminal 13 amino acids of nonactive GIP (GIP(3-15)) were used as antigen (2) for measurement.

2) Immunization

Three BALB/c mice were used and each immunized by subcutaneous administration to the back. For priming, an emulsion of the thus-prepared antigen mixed with a complete Freund's adjuvant was administered. After the priming, a booster was carried out using an emulsion of the antigen mixed with an incomplete Freund's adjuvant every two weeks. The amount of the antigen used in one immunization was in the range of 0.1 to 0.2 mg. Seven weeks after the priming, antibody titer measurement was carried out using serum collected from each mouse to confirm elevation in antibody titer.

3) Cell Fusion

The spleen was harvested from the mouse having an elevated antibody titer to obtain spleen cells. The obtained spleen cells were fused with a mouse myeloma cell line P3U1 by the PEG method. Then, the fused cells were inoculated ($1 \times 10^5$ cells/well) to twenty 96-well plates.

4) Screening

The antigens (1) and (2) for measurement were each diluted to 1 µg/mL with PBS(−) and immobilized onto plates. The reaction of the hybridoma culture supernatants with the antigens (1) and (2) was evaluated by ELISA using a HRP-labeled anti-mouse Ig antibody as a secondary antibody to select a hybridoma which exhibited positivity for the antigen (1) and negativity for the antigen (2), as an anti-active GIP monoclonal antibody-producing hybridoma.

5) Cloning

The hybridoma thus obtained was cultured such that a single colony was obtained by the limiting dilution method. In this way, the antibody-producing hybridoma was cloned. A well in which a single colony was formed was measured again by ELISA to establish a 9B9H5-B9 line producing an antibody which exhibited positivity for the antigen (1) and negativity for the antigen (2).

In order to preserve the obtained antibody-producing hybridoma, the hybridoma was cultured, recovered at the logarithmic growth phase, then adjusted to a cell concentration of $1 \times 10^6$ cells/mL with a FBS-containing cell-freezing solution, then dispensed at $1 \times 10^6$ cells/tube to freezing tubes, and preserved at −80° C. in BICELL.

6) Antibody Production

The obtained antibody-producing hybridoma in the frozen vials was revived and conditioned in a serum-free medium Hybridoma-SFM. After culture multiplication, the hybridoma was cultured in two roller bottles (500 mL×2, 1 L), and the culture supernatant was recovered. The recovered culture supernatant was used in protein A purification to purify a monoclonal antibody.

Example 2 Reactivity with Active GIP in ELISA

The reactivity of the monoclonal antibody obtained in Example 1 with active GIP was confirmed by ELISA. The amino group of the anti-active GIP monoclonal antibody was biotinylated using a $NH_2$ group biotinylation kit (manufactured by Dojindo Laboratories). ELISA was conducted using 1 µg/mL prepared biotinylated anti-active GIP monoclonal antibody instead of a detection antibody 'GIP detection antibody' (biotinylated anti-total GIP monoclonal antibody) included in Human (total) GIP ELISA kit (manufactured by Merck Millipore). Six 4-fold serial dilutions (8.2 to 2000 pg/mL) were prepared with a 2000 pg/mL solution of GIP(1-42) or GIP(3-42) as the highest concentration. The capture antibody used was an anti-total GIP monoclonal antibody (included in the Human GIP (total) ELISA kit manufactured by Merck Millipore). The detection antibody used was the biotinylated anti-active GIP monoclonal antibody. A sandwich ELISA system containing a peroxidase-streptavidin conjugate was used in detection. GIP concentrations were plotted on the X axis against absorbance of 450 nm to 590 nm on the Y axis to prepare a calibration curve (FIG. 1).

Figure 1:
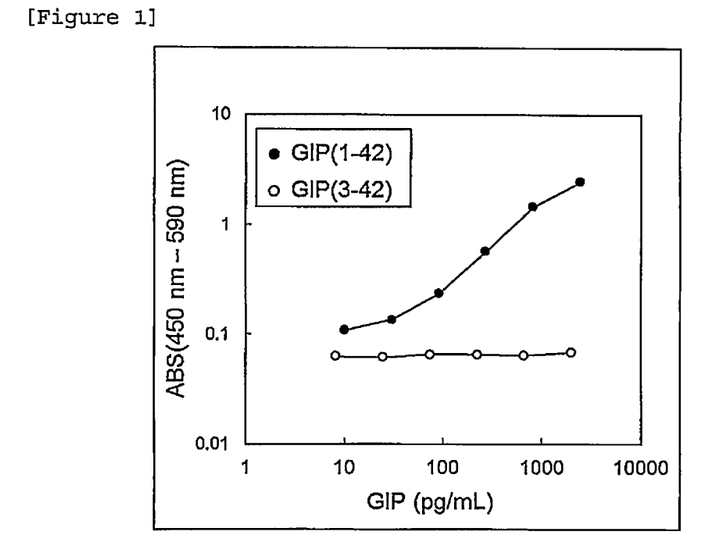
FIG. 1 shows a calibration curve prepared by sandwich ELISA using the anti-active GIP antibody of the present invention.

As shown in FIG. 1, the absorbance did not rise even in a high-concentration range of GIP(3-42), whereas the absorbance rose in a concentration-dependent manner only for GIP(1-42). Therefore, this ELISA system was confirmed to be able to specifically detect GIP(1-42) without causing cross-reactivity with GIP(3-42).

Example 3 Measurement of Human Active GIP

The GIP(1-42) ELISA method constructed in Example 2 was evaluated for whether or not this method could actually be used in the measurement of GIP(1-42) in human blood. For this purpose, the study was conducted using a human plasma sample.

Figure 2:
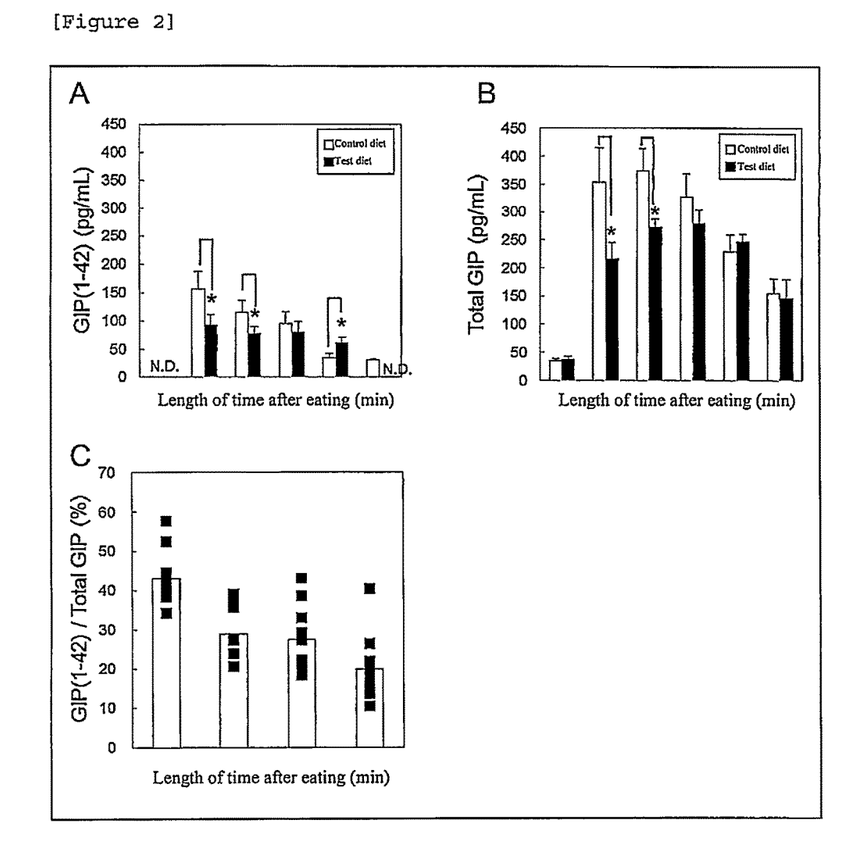
FIG. 2 shows results of quantifying active GIP in healthy human blood using the anti-active GIP antibody of the present invention.

Healthy individuals took a control diet (standard diet) or a test diet (low-GIP diet). A GIP(1-42) level in blood measured at each point of time thereafter is shown in FIG. 2A, and a total GIP level in blood measured for comparison is shown in FIG. 2B. The GIP(1-42) level in blood was confirmed to reach its peak 30 minutes after eating (FIG. 2A), suggesting that the concentration in blood is decreased early as compared with total GIP which maintained a high level up to 120 minutes after eating (FIG. 2B). When the control diet and the test diet were compared, significant decrease in the GIP(1-42) level in blood was confirmed 30 minutes and 60 minutes after eating for the test diet with respect to the control diet (FIG. 2A). Thus, similar tendency as in the total GIP level (FIG. 2B) was found. The ratio of GIP(1-42) to total GIP after eating was determined (FIG. 2C). Average values at 30, 60, 120, and 180 minutes after eating were 43%, 28%, 27%, and 19%, respectively, suggesting that the proportion of the active GIP is high at an early stage after eating and is then decreased over time.

Example 4 Epitope Analysis of Anti-Active GIP Monoclonal Antibody

In order to identify an epitope for the monoclonal antibody prepared in Example 1, the following synthetic peptides were prepared;

(1) GIP(1-10): NH2-YAEGTFISDY-COOH (SEQ ID NO:12);

(2) GIP(1-9): NH2-YAEGTFISD-COOH (SEQ ID NO:13);

(3) GIP(1-8): NH2-YAEGTFIS-COOH (SEQ ID NO:14);

(4) GIP(1-7): NH2-YAEGTFI-COOH (SEQ ID NO:15);

(5) GIP(1-6): NH2-YAEGTF-COOH (SEQ ID NO:16);

(6) GIP(1-6)+GIP nonspecific 4aa (random 4aa): NH2-YAEGTFVNLV-COOH (SEQ ID NO:17).

The synthesized 6 peptides were each diluted to 1 µg/mL with PBS(−) and immobilized onto 96-well plates. ELISA was conducted using the biotinylated anti-active GIP monoclonal antibody and a peroxidase-streptavidin conjugate for detection. The results are shown in FIG. 3.

Figure 3:
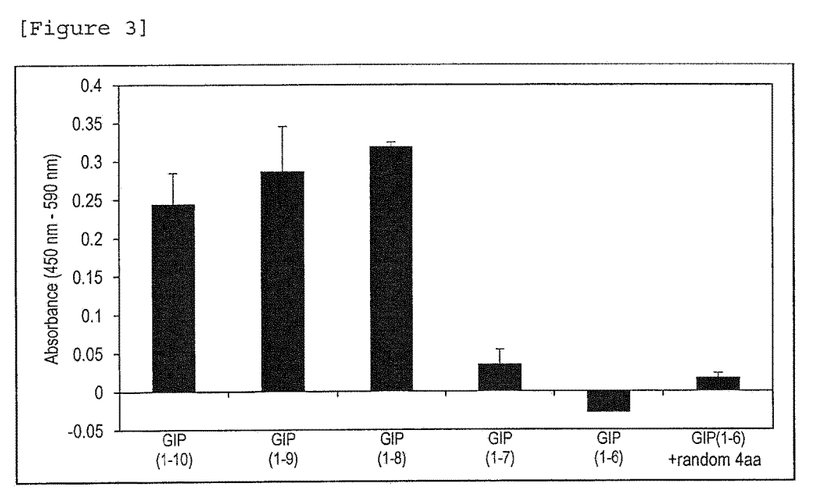
FIG. 3 shows results of epitope analysis of the anti-active GIP antibody of the present invention.

FIG. 3 demonstrated that GIP(1-8) or larger peptides, i.e., active GIP peptides having a length of N-terminal 8 or more amino acids, are necessary as a recognition site of the anti-active GIP monoclonal antibody.

Example 5 Analysis of Amino Acid Sequences of H Chain and L Chain Variable Regions (1) Sequencing Total RNA was extracted from the 9B9H5-B9 hybridoma according to a routine method. cDNA was prepared by using this total RNA as a template. PCR products comprising genes encoding H chain and L chain variable regions were amplified by PCR using the primers shown in Table 1 under the conditions shown in Table 2.

More specifically, RACE PCR reaction was performed by using the obtained cDNA (synthesized with an H chain-specific primer) as a template, a mouse antibody (IgG) H chain-specific primer as a reverse primer, and the universal primer shown in Table 1 as a forward primer. Similarly, RACE PCR reaction was performed by using the cDNA (synthesized with an L chain-specific primer) as a template and an L chain-specific primer. The PCR enzyme used was PrimeSTAR GXL. The obtained PCR products were ligated with a cloning plasmid pMD20-T, and 48 clones were obtained per PCR product by a routine method of transformation.

TABLE 1

| Purpose | Primer name | Nucleotide sequence (5'→3') | SEQ ID NO |
|---|---|---|---|
| Forward primer | Universal primer | ctaatacgactcactatagggcaagcagtggtatcaacgcaga | 6 |
| | | gtctaatacgactcactagggc | |
| Reverse primer | H-PCR* | gggaartarcccttgaccaggca | 7 |
| | | gggaartagccttttgacaaggca | 8 |
| | L-PCR | cactgccatcaatcttccacttgaca | 9 |

*H-PCR was used as an equimolar mixture of the two sequences shown.

TABLE 2

RACE PCR reaction composition

| | |
|---|---|
| H₂O | 26.5 µl |
| 5 × PrimeSTAR GXL Buffer (Mg²⁺ plus) | 10 µl |
| dNTP (2.5 mM each) | 4 µl |
| PrimeSTAR GXL DNA Polymerase | 1 µl |
| cDNA | 2.5 µl |
| 10 × Universalprimer | 5 µl |
| H-PCR or L-PCR primer (10 µM) | 1 µl |
| Total volume | 50 µl |

RACE PCR reaction cycle

| | |
|---|---|
| 94° C., 10 sec | |
| 98° C., 10 sec<br>60° C., 15 sec<br>68° C., 1 min | 30 Cycles |
| 68° C., 3 min | |

The obtained clones were unilaterally analyzed from the plasmid regions using a primer M13-47 (cgccagggttttccca-gtcacgac: SEQ ID NO: 10). Sequencing was performed using Big Dye Terminators v3.1 cycle sequencing kit (Applied Biosystems, Inc. (ABI)) according to the attached protocol to determine the sequences. Among the determined sequences, amino acid sequences presumed from nucleotide sequences derived from the experimental samples were subjected to homology search using BLAST (blast.ncbi.nlm.nih.gov/Blast.cgi) to determine the putative nucleotide sequences (start codon and downstream sequences) encoding the H chain and L chain variable regions, and the amino acid sequences thereof (SEQ ID NOs: 1 to 4). In this context, the nucleotide sequence encoding the H chain variable region of the monoclonal antibody and the amino acid sequence thereof are shown in SEQ ID NOs: 1 and 2, respectively. The nucleotide sequence encoding the L chain variable region of the monoclonal antibody and the amino acid sequence thereof are shown in SEQ ID NOs: 3 and 4, respectively.

As a result of conducting the homology search of the amino acid sequence of the H chain variable region using BLAST (blast.ncbi.nlm.nih.gov/Blast.cgi), a polypeptide having an amino acid sequence having 90% or higher identity to its amino acid residues "EMNPSDGRTHFNE" from positions 50th to 62th position from the N terminus was not found.

The invention claimed is:

1. An anti-active gastric inhibitory polypeptide (GIP) antibody that binds to active GIP and does not substantially bind to nonactive GIP,
   the antibody recognizing at least one or more amino acids selected from the group consisting of the amino acids at the 8th to 10th position of the amino acid sequence of SEQ ID NO: 5,
   wherein the antibody comprises,
   as an H chain variable region, a region comprising the amino acid sequence of SEQ ID NO: 2 or a conservative modification thereof having at least 95% identity to SEQ ID NO:2, and,
   as an L chain variable region, a region comprising the amino acid sequence of SEQ ID NO:4 or a conservative modification thereof having at least 95% identity to SEQ ID NO:4.

2. The antibody according to claim 1, wherein the antibody comprises, as an H chain variable region, a region comprising the amino acid sequence of SEQ ID NO: 2.

3. The antibody according to claim 1, wherein the antibody comprises, as an H chain variable region, a region comprising the amino acid sequence of a conservative sequence modification of SEQ ID NO:2 that has 98% or higher identity to the amino acid sequence of SEQ ID NO: 2.

4. The antibody according to claim 1, wherein the antibody comprises, as an L chain variable region, a region comprising the amino acid sequence of SEQ ID NO: 4.

5. The antibody according to claim 1, wherein the antibody comprises, as an L chain variable region, a region comprising the amino acid sequence of a conservative sequence modification of SEQ ID NO:4 that has 98% or higher identity to the amino acid sequence of SEQ ID NO: 4.

6. A method for detecting or measuring active GIP, the method comprising bringing the anti-GIP antibody of claim 1 into contact with a specimen and detecting binding of active GIP that was in the specimen to the antibody.

7. A method for detecting or measuring active GIP in a sample, comprising the following steps 1) and 2):
   1) contacting an anti-GIP antibody according to claim 1 that is labeled and an anti-GIP antibody that is immobilized, either together or separately, with a sample-containing solution; and
   2) measuring the amount of the label in a complex formed by the active GIP in the sample, the immobilized anti-GIP antibody, and the labeled antibody of claim 1.

8. A reagent for detection or measurement of active GIP, comprising the antibody according to claim 1.

9. The antibody according to claim 1, wherein the antibody comprises, as an H chain variable region, a region comprising the amino acid sequence of SEQ ID NO: 2, and as an L chain variable region, a region comprising the amino acid sequence of SEQ ID NO: 4.

10. A method for detecting or measuring active GIP, the method comprising bringing the anti-GIP antibody of claim 9 into contact with a specimen and detecting binding of active GIP that was in the specimen to the antibody.

11. A method for detecting or measuring active GIP in a sample, comprising the following steps 1) and 2):
   1) contacting an anti-GIP antibody according to claim 9 that is labeled and an anti-GIP antibody that is immobilized, either together or separately, with a sample-containing solution; and
   2) measuring the amount of the label in a complex formed by the active GIP in the sample, the immobilized anti-GIP antibody, and the labeled antibody of claim 9.

12. A reagent for detection or measurement of active GIP, comprising an antibody according to claim 9.

13. The antibody according to claim 1, wherein the antibody comprises, as an H chain variable region, a region comprising the amino acid sequence of a conservative sequence modification of SEQ ID NO: 2 that has 98% or higher identity to the amino acid sequence of SEQ ID NO: 2, and the amino acid sequence of a conservative sequence modification of the amino acid sequence of SEQ ID NO: 4 that has 98% or higher identity to the amino acid sequence of SEQ ID NO: 4.

* * * * *